United States Patent [19]

Leight

[11] 4,094,315
[45] June 13, 1978

[54] EAR PLUG

[76] Inventor: Charles Leight, 118 S. Orlando Ave., Los Angeles, Calif. 90048

[21] Appl. No.: 736,885

[22] Filed: Oct. 29, 1976

[51] Int. Cl.² ............................................. A61F 11/02
[52] U.S. Cl. ..................................... 128/152; 128/341; 128/343
[58] Field of Search .............. 128/151, 152, 127, 130, 128/131, 341, 343; 215/DIG. 3, 296, 358, 360, 362

[56] References Cited

U.S. PATENT DOCUMENTS

| 3,123,069 | 3/1964 | Laisne et al. | 128/152 |
| 3,259,128 | 7/1966 | Leight | 128/152 |

FOREIGN PATENT DOCUMENTS

| 1,947,740 | 5/1971 | Germany | 128/152 |
| 418,326 | 10/1934 | United Kingdom | 128/127 |

*Primary Examiner*—Robert W. Michell
*Assistant Examiner*—Henry J. Recla
*Attorney, Agent, or Firm*—Fulwider, Patton, Rieber, Lee & Utecht

[57] ABSTRACT

A sound-reducing ear plug formed of a soft plastic and adapted to fit into ear canals of different sizes.

1 Claim, 4 Drawing Figures

.050 WALL, FLARE THICKNESS TO .065

EAR PLUG

BACKGROUND OF THE INVENTION

In recent years, it has become increasingly apparent that excessive noise produces both short term and long term undesirable effects on those subjected to it. Thus, a high level noise for a short time will increase fatigue and worker irritability, and the long term effects can be partial or total deafness. Recognition of the problem has led to requirements by safety authorities that either call for the reduction of the noise itself, or the provision of protective means such as ear plugs that reduce the effect of the noise.

Any number of different forms of ear plugs have been developed, ranging from the very early use of fibers such as cotton, through soft wax, to various forms of molded plugs formed of materials of varying degrees of hardness. The molded plugs, formed in various shapes, have had various advantages and disadvantages. Aside from the problem of providing sufficient attenuation of the sound, most of the prior plugs have suffered from one or more disadvantages, including ease or difficulty of insertion, adaptability to ear canals of differing size, cleanliness and other problems.

Where the plugs are required by the various safety authorities, it is a real problem for the employer to insure that all of the workers in the noisy areas wear the plugs at all times when they should. If the plugs are not easily installed or are not comfortable, many workers will refuse, or conveniently forget to insert the plugs. In those instances where the worker is working with dirty or abrasive material, wax plugs that must be molded to the ear are quite impractical, since they tend to pick up the dirty or abrasive material and force it into the ear. Additionally, where the employer furnishes the ear plugs, the quantity of plugs that must be furnished is such that cost becomes an important factor.

SUMMARY OF THE INVENTION

The present invention relates to an ear plug of soft, resilient, and generally tubular construction that is easily inserted by the worker after only the barest minimum of instruction, the plug being such as to comfortably fit in ear canals of different sizes so that generally only a single size ear plug need by provided for all workers. The body of the plug is of stepped construction so that a good seal between the plug and the ear canal is provided, and the wall thickness is varied to produce a balance of desired resilience and strength. The flared outer end of the plug aids in the insertion and removal of the plug, and the use of a suitable plastic type material permits the plug to be made at a very low cost.

DESCRIPTION OF PREFERRED FORM

Figure 1:
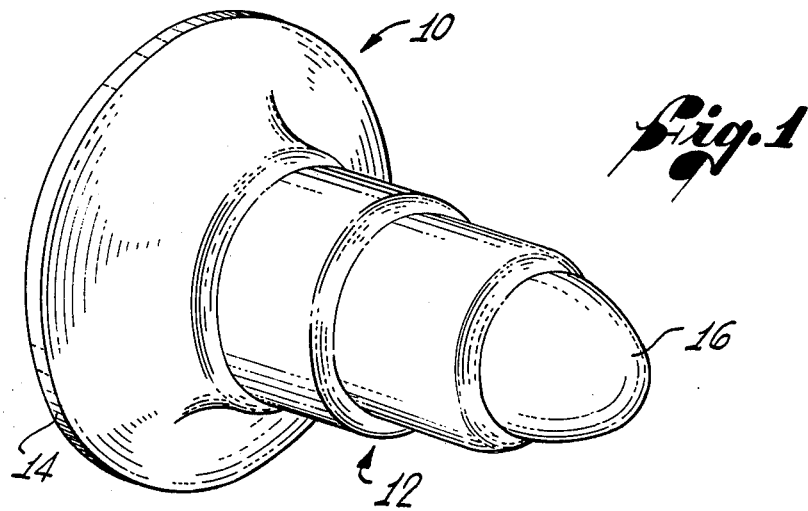
FIG. 1 is an enlarged perspective view of an ear plug looking from the small end that is inserted into the ear canal toward the large flanged end.
Figure 2:
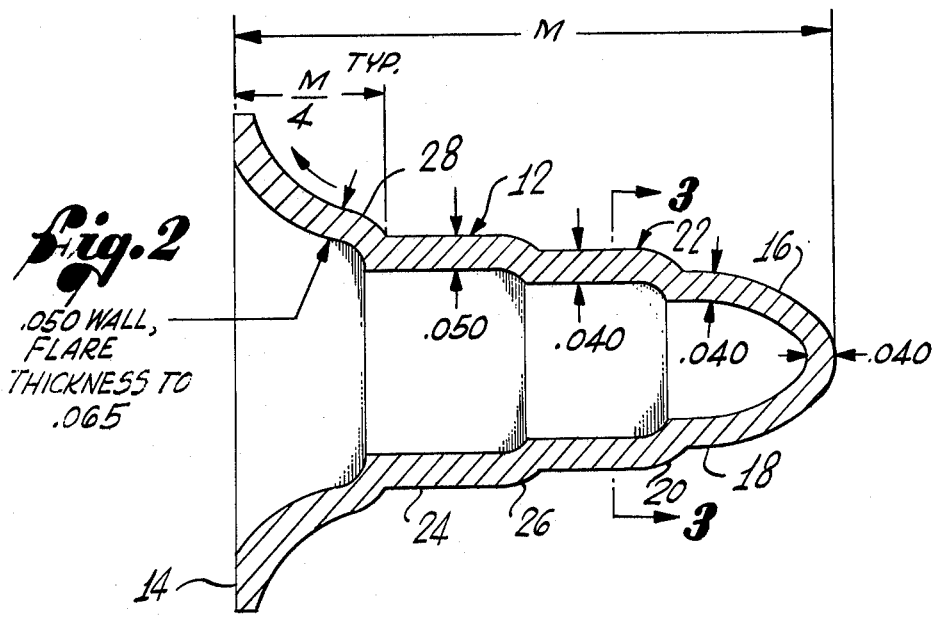
FIG. 2 is an axial sectional view of the ear plug shown in FIG. 1.

As best indicated in FIGS. 1 and 2, the ear plug 10 consists of a stepped cylindrical body member 12 closed at one end and having a conical member or flange 14 at the other end. The body 12 is hollow with a wall thickness that is thinnest at the closed end of the body and thickest at the flange 14. While various materials may be used, it has been found that soft resilient materials, such as silicone, neoprene, polyvinyl chloride, or other suitable plastic materials are eminently satisfactory.

The closed end 16 of the body 12 has a generally bullet shape and, by way of example, the maximum external diameter of this section 16 taken at the point 18 may suitably be 0.290 inches. At this point 18 the end 16 is substantially cylindrical and the cylinder merges into an ellipsoid to form the closed portion of the end. This cylindrical-ellipsoidal end portion 16 is the portion of the ear plug that fits farthest into the ear canal and hence, for convenience, is hereinafter referred to as "the inner end."

Adjacent the point 18 and away from the ellipsoidal portion is a transition section 20 in the form of a curved portion that extends from the smaller diameter cylinder at 18 to antermediate diameter portion at 22. The smaller cylindrical portion 18 may, by way of example, have an external diameter of 0.290 inches, while the intermediate cylindrical portion 22 may, by way of example, have an external diameter of 0.370 inches, while the curved transition section 20 has an external surface formed as an arc having a radius of curvature, by way of example, of 0.120 inches. The end 16 and cylindrical portion 18, the transition portion 20, and intermediate cylindrical portion 22 all have a wall thickness of, by way of example, 0.040 inches, and it will be appreciated that the transition portion 20 acts to provide a certain amount of stiffening for the body portion 12, so that while the cylindrical portions 18 and 22 are soft and easily conformed to the shape of the ear canal, the transition portion 20 provides stiffness so that the body does not collapse.

Between the intermediate cylindrical portion 22 and the flange 14, there is a larger cylindrical portion 24 that is joined to the intermediate cylindrical portion by a transition section 26 corresponding to the transition section 20. Like the transition section 20, the transition section 26 may, by way of example, have an outer surface whose radius of curvature is 0.120 inches and also, by way of example, the diameter of the larger cylindrical portion 24 may have a diameter of 0.420 inches.

At the outer end of the larger cylindrical portion 24, there is another transition section 28 formed like the transition sections 20 and 26 as an arc having a radius of curvature of 0.120 inches, by way of example, and the wall of the larger cylindrical section 24 and appropriate portions of the transition sections 26 and 28 are approximately 0.050 inches thick, by way of example. The increased thickness of the largest cylindrical section 24 provides a corresponding stiffness, so that the wall of the largest cylindrical section does not collapse. The graded wall thickness and the transition sections 20, 26 and 28 all cooperate with the end section 16 and the small, intermediate and large cylindrical sections to provide an ear plug having a soft and reslient construction, but one resisting collapse so that the plug may be inserted into the ear canal and make a sealing fit therewith without hurting or damaging any of the ear structure.

As previously mentioned, the conical flange 14 formed at the outermost end of the ear plug forms a convenient means for extracting the plug from the ear canal; and to provide additional strength for this purpose, the thickness of the wall of the flange is flared from that at the transition section 28. Thus, where the wall thickness may, by way of example, be 0.050 inches at the transition secton 28, it can conveniently flare or increase in thickness to 0.065 inches at the thickest portion of the flange. As indicated, of course, the outer edge of the flange may be trimmed to provide a finished appearance.

By way of example, the over all length of the ear plug is, of course, intended to be in proportion to the size of the ear and the ear canal into which it is to fit, and it has been found, by way of example, that an ear plug having an over all length of approximately one inch from the outermost surface of the flange 14 to the closed tip of the end 16 is quite suitable. This dimension is conveniently divided into four equal portions, with the distance from the outer surface of the flange 14 to the junction of the large cylindrical portion 24 and the transition section 28 occupying one-fourth of the length, the distance from the junction of the large cylinder 24 and transition section 28 to the junction of the intermediate cylinder 22 and the transition 26 being another quarter of the length. The distance from the junction of the intermediate cylinder 22 and the transition section 26 to the junction of the small cylinder 18 and the transition section 20 can be another quarter of the distance, and this leaves a quarter of the distance for the small cylinder and end 16. The maximum distance of the flange 14 may conveniently be 0.812 inches.

Figure 4:
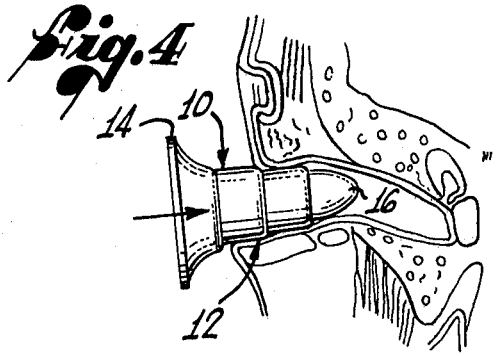
FIG. 4 is a view indicating how an ear plug is inserted into the ear canal to make a sealing fit therewith.
Figure 3:
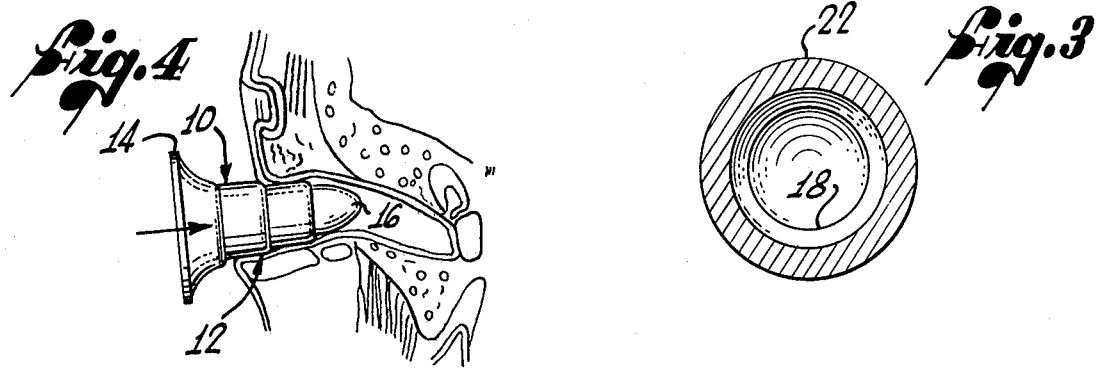
FIG. 3 is a cross-sectional view taken on the line 3 — 3 of FIG. 2 and indicating the symmetrical construction of the plug.

To install the ear plug 10 in the ear canal, as indicated in FIG. 4, the flange 14 is grasped and the tip 16 is inserted into the canal, all as generally indicated in FIG. 4. The index finger is then inserted into the interior of the ear plug into the central cavity, and by then pressing inwardly with the finger and at the same time wiggling the tip of the finger from side to side, the ear plug is urged into the ear canal to make a sealing fit therewith as indicated in FIG. 4.

To remove the ear plug it is only necessary to grasp the flange 14 between the thumb and index finger and gently pull it out, so that the entire ear plug is removed from the ear canal.

It will be appreciated that the ear plug shown and described herein is fully capable of fitting substantially all ears. The plug has good sound attenuating characteristics and does not create a pressure within the ear canal, so that an unnatural and uncomfortable condition is created. The ear plug can be worn with comfort for a long period of time and the construction is such that the body of the ear plug need not be touched by hand, so that the chances of contamination of the body are greatly reduced. Furthermore, while the plug can be re-used a number of times, it is of sufficiently inexpensive construction that new plugs can be provided whenever the old plug is lost or contaminated.

It is to be understood that more or fewer cylindrical sections may be provided in an ear plug, and thus there may be two, three, four, or five such sections. However, there is a practical limit to the number of sections, since each section must be long enough to contribute to the sealing effect, and the over all length must not exceed the length of the ear canal.

It will be appreciated that while a preferred form of the invention has been shown, modifications may be made therein and consequently, the invention is not to be limited to the particular form or arrangement of parts herein shown and described, except as limited by the following claims.

I claim:

1. An ear plug for insertion into an ear canal which includes:

a plurality of hollow cylindrical members of progressively larger diameters sizes, the smallest of said cylinders being closed at its free end, and each cylinder being connected to the next larger cylinder by a transition member;

the wall thickness of said cylindrical members being varied from the thinnest in said smallest cylinder to the thickest in said largest cylinder; and a hollow conical member open at both ends with its smaller end connected to the largest of said cylindrical members by a transition member, said conical member having a thickness greater than any of said cylindrical members and a mechanical strength sufficient to enable it to be grasped to remove said ear plug from the ear whereby, the wall thickness of said cylindrical members is such as to prevent the collapse of said cylindrical members while permitting said cylindrical members to conform to the shape of an ear canal and said transition members act to stiffen said cylindrical members.

* * * * *

UNITED STATES PATENT AND TRADEMARK OFFICE
CERTIFICATE OF CORRECTION

PATENT NO. : 4,094,315
DATED : June 13, 1978
INVENTOR(S) : Charles Leight

It is certified that error appears in the above-identified patent and that said Letters Patent are hereby corrected as shown below:

Column 3, line 28,

After the word "diameters", delete--sizes--;

Signed and Sealed this

Nineteenth Day of June 1979

[SEAL]

Attest:

RUTH C. MASON
Attesting Officer

DONALD W. BANNER
Commissioner of Patents and Trademarks